US012655269B2

(12) United States Patent
Kottari et al.

(10) Patent No.: US 12,655,269 B2
(45) Date of Patent: Jun. 16, 2026

(54) ADDITIVE COMPOUND FOR WARM MIX ASPHALT AND PROCESS OF SYNTHESIS THEREOF

(71) Applicant: HINDUSTAN PETROLEUM CORPORATION LIMITED, Bengaluru (IN)

(72) Inventors: Naresh Kottari, Bengaluru (IN); Sandip Bhowmik, Bengaluru (IN); Venkatesan Santhanam, Bengaluru (IN); Ravi Balasubramaniam, Bengaluru (IN)

(73) Assignee: HINDUSTAN PETROLEUM CORPORATION LIMITED, Bengaluru (IN)

( * ) Notice: Subject to any disclaimer, the term of this patent is extended or adjusted under 35 U.S.C. 154(b) by 335 days.

(21) Appl. No.: 18/268,461

(22) PCT Filed: Apr. 13, 2021

(86) PCT No.: PCT/IN2021/050367
§ 371 (c)(1),
(2) Date: Jun. 20, 2023

(87) PCT Pub. No.: WO2022/180638
PCT Pub. Date: Sep. 1, 2022

(65) Prior Publication Data

US 2024/0309178 A1 Sep. 19, 2024

(30) Foreign Application Priority Data

Feb. 26, 2021 (IN) ............................ 202141008203

(51) Int. Cl.

| | |
|---|---|
| ***C07C 231/00*** | (2006.01) |
| ***C07C 231/02*** | (2006.01) |
| ***C07C 231/24*** | (2006.01) |
| ***C07C 233/36*** | (2006.01) |
| ***C08K 5/20*** | (2006.01) |
| ***C08L 95/00*** | (2006.01) |

(52) U.S. Cl.
CPC .............. *C08K 5/20* (2013.01); *C07C 231/02* (2013.01); *C07C 231/24* (2013.01); *C07C 233/36* (2013.01); *C08L 95/00* (2013.01); *C08L 2555/24* (2013.01)

(58) Field of Classification Search
CPC ........ C08K 5/20; C08K 5/175; C07C 231/02; C07C 231/24; C07C 233/36; C08L 95/00; C08L 2555/24; Y02A 30/30; E01C 7/265
See application file for complete search history.

(56) References Cited

U.S. PATENT DOCUMENTS 8,440,011 B2 5/2013 Naidoo et al.
8,840,717 B2 9/2014 Naidoo et al.
2010/0319577 A1* 12/2010 Naidoo .................. C08L 91/06 106/500
2013/0197134 A1 8/2013 Leal et al.
2013/0239850 A1 9/2013 Naidoo et al.
2016/0376440 A1 12/2016 Naidoo et al.
2023/0140457 A1 5/2023 Gutiérrez Muñiz et al.

FOREIGN PATENT DOCUMENTS

KR 101505829 B1 * 3/2015 ............. C08L 23/04
WO 2009062925 A1 5/2009
WO WO-2012139180 A1 * 10/2012 ............. C08L 95/00
WO 2018189570 A1 10/2018

OTHER PUBLICATIONS

Butler et al. Sequential nature of the thermal reaction of stearic acid with some 1,2-diamines, J. Chem. Soc., Perkin Trans. 1, 386-389 (Year: 1976).*
KR_101505829_B1_Machien Translation (Year: 2015).*
Butler Richard et al."Sequential nature of the thermal reaction of stearic acid with some 1,2-diamines" Journal of the Chemical Society, Perkin Transactions 1, Jan. 1, 1976 Royal Society of Chemistry, Cambridge, UK; Nr:4,p. 386; XP055860276.
Morea et al., "Rheological properties of asphalt binders with chemical tensoactive additives used in Warm Mix Asphalts (WMAs)" Constr. Build. Mater., vol. 29, 2012, pp. 135-142.
Pérez-Martínez et al. "Analysis of cleaner technologies based on waxes and surfactant additives in road construction", Journal of Cleaner Production (J. Clean. Prod., 65 (2014), pp. 374-379).
Pereira Raul et al. "Warm mix asphalt: Chemical additives' effects on bitumen properties and limestone aggregates mixture compactibility" International Journal of Pavement Research and Technology, May 1, 2018; vol. 11, Nr:3, pp. 285-299; XP055781495.
International Search Report issued in International Application No. PCT/IN2021/050367.
Written Opinion issued in International Application No. PCT/IN2021/050367.

* cited by examiner

*Primary Examiner* — Amber R Orlando
*Assistant Examiner* — Anastasia A. Kuvayskaya
(74) *Attorney, Agent, or Firm* — The Belles Group, P.C.

(57) ABSTRACT

The present invention provides additive compound for warm mix asphalt (WMA) for the paving of road surfaces, whereby the additive compounds facilitate the mixing, lay down and compaction of asphalt mixes at low temperatures while retaining the mechanical properties of the asphalt composition. Further, the present invention provides a process of synthesis of the additive compounds. Additionally, the present invention provides a warm mix asphalt formulation involving the additive compounds and a method of preparation thereof. The chemical additives of the present invention are liquid surfactants that ensure reduction of internal friction during manufacturing, and subsequently formulations comprising these chemical additives results in reduction of compaction temperature of the bituminous mixtures.

12 Claims, No Drawings

ADDITIVE COMPOUND FOR WARM MIX ASPHALT AND PROCESS OF SYNTHESIS THEREOF

CROSS-REFERENCE TO RELATED PATENT APPLICATIONS

The present application is a U.S. national stage application under 35 U.S.C. § 371 of PCT/IN2021/050367, filed Apr. 13, 2021, which claims priority to Indian Patent Application number 202141008203 filed on Feb. 26, 2021. The disclosures of the aforementioned priority applications are incorporated herein by reference.

FIELD OF THE INVENTION

The present invention relates to additive compound for warm mix asphalt (WMA) for the pavement of road surfaces that facilitates the mixing, lay down and compaction of asphalt mixes at low temperatures while retaining the mechanical properties of the asphalt composition. Further, the present invention relates to a process of synthesis of the additive compounds. Additionally, the present invention relates to a warm mix asphalt formulation involving the additive compounds and a method of preparation thereof.

BACKGROUND OF THE INVENTION

Asphalt mixes are widely used in road construction and maintenance and the majority of asphalt mixes that are used currently are produced by the hot method which is generally known as hot-mix or HMA (Hot Mix Asphalt) and also known as asphalt concrete. These asphalt mixes consist of asphalt binder and mineral aggregate. The aggregates used could be either natural or processed. The aggregates are usually a mixture of various sizes to give desired load bearing strength and properties to the asphalt mix as specified in the mix design. Asphalt mixtures are the most widely used material in the construction of roads. The regular HMA requires high manufacturing temperature (around 160° C.), which is associated with the release of a large volume of greenhouse gases. One of the causes of pollution associated with the construction of transportation infrastructures is the emission of greenhouse gases into the atmosphere. Thus, in order to limit these problems, a cleaner production of bituminous mixtures is required to decrease the manufacturing temperature without reducing their mechanical behavior. One possible alternative is the use of Warm Mix Asphalt (WMA), which is manufactured at a temperature much lower than the conventional Hot Mix Asphalt (HMA). It was shown before that the use of WMA in pavements for roads allows for lower emissions, fumes and odors; with a reduction of ageing of the bitumen. The lower mixing and paving temperatures, obtained by the use of Warm Mix Asphalt, minimize fume and odour emissions and creates cooler working conditions for the asphalt workers. Thus, the release of fume is reduced by around 50% for each 12° C. reduction in temperature. Warm-Mix Asphalt (WMA) technologies operate above 100° C., so the amount of water remaining in the mix is very small. Various techniques are used to reduce the effective viscosity of the binder enabling full coating and subsequent compactability at lower temperatures. Different organic additives can be used to lower the viscosity of the binder (bitumen) at temperatures above about 90° C. A commonly used additive is a special paraffin wax produced by conversion of natural gas. Organic additives typically give a temperature reduction of between 20-30° C. whilst they also improve the deformation resistance of asphalt so modified. Chemical additives act as surfactants at the microscopic interface of the aggregates and the bitumen. They regulate and reduce the frictional forces at that interface at a range of temperatures, typically between 140° C. and 85° C. and facilitate reduction of compaction temperature. Further, a range of foaming techniques is applied to reduce the viscosity of bitumen. Various means are employed to introduce small amounts of water into the hot bitumen. The water turns to steam, increases the volume of the bitumen and reduces its viscosity for a short period.

The use of Warm Mix Asphalt has several advantages, not only for the asphalt mix itself but also for the manufacturing process. Lower asphalt temperatures result in less hardening of the bitumen/binder during manufacture and lower production temperatures reduce the thermal stress on the plant components. Employing the various technologies for reduction of effective viscosity, WMA can be compacted at a temperature lower than conventional HMA for an equivalent degree of compaction. Further reduction of the production temperature in the WMA and Half Warm Asphalt processes do lead to significant reductions of stack emissions. The reduced fuel and energy usage gives a reduction of the production of greenhouse gases and reduces the $CO_2$/Carbon footprint. The reduction in production of fumes result in a subsequent reduction of workers' potential for exposure to fugitive emissions from the plant. Moreover, because warm mix asphalt is manufactured and shipped at lower temperatures, it does not cool as fast as its hotter counterpart. Therefore, it can be shipped over longer distances and used outside of the normal paving and road construction for months. It can be used to pave roads, highways, interstates, cart paths, driveways and walking paths during the day or at night.

Among the several processes and products introduced into the market to reduce compaction and mix temperatures, a great deal of research provided that the performance of bituminous mixtures modified with chemical additives is generally superior to the conventional one. Morea et al. (Constr. Build. Mater., 29 (2012), pp. 135-142) verified that the incorporation of chemical additives improves the elastic response of bitumen, a fact observed through a frequency sweep test at low frequencies. Additionally, these additives allowed to reduce the accumulated strain in the end of creep test compared to unmodified bitumen. Pérez-Martinez et al. (J. Clean. Prod., 65 (2014), pp. 374-379) found that chemical additives, if applied through wet process provide better results, producing mixtures at lower temperatures but ensuring comparable or even superior mechanical behaviour to conventional mixtures. These authors through rheological tests showed that bitumen modified with chemical additives exhibited an improvement of fatigue resistance at medium temperatures. Moreover, these modified bitumen exhibited higher values of surface free energy which could mean better adhesion between the mixture components and, consequently, higher resistance to water action.

US 20160376440A1 discloses an asphalt additive comprising an oil component comprising vegetable oil and/or a crude tall oil, an amine component, and an organosilane component. Further, the patent application discloses asphalt compositions and products comprising asphalt binder, aggregate, and the additive, and treatment methods include contacting asphalt compositions or asphalt products with the additive.

WO 2009/062925A1 discloses an additive package for warm-mix asphalt formulations for the pavement of road surfaces, said additive package comprising a) surfactant component, and b) an asphalt rheology modifying component, wherein said asphalt rheology modifying component comprises at least one of: i) a wax component and ii) a resin component. The patent application also relates to a warm mix asphalt having improved compaction at lower temperatures, and to a pavement made from said warm mix asphalt.

Although, the utility of chemical additives for reduction of compaction temperature of warm mix asphalt compositions has been studied by different groups, yet there remains an unmet need for the development of such compositions involving new chemical additive that would exert effect on the viscosity of the bitumen also when formulated in the suitable ratio. Further, in addition to solving these technical problems, it is also necessitated to provide a composition that improves moisture resistance of the hot-mix asphalt used for production of road surfaces without sacrificing the performance characteristics of the asphalt mix. So, developments of cost effective warm mix asphalt compositions based on chemical additives are highly desired for paving of roads without causing any significant amount of environmental pollution.

OBJECTIVES OF THE INVENTION

The prime objective of the present invention is to provide chemical entities that serve as suitable additives for warm mix asphalts used in paving of roadways.

Another objective of the present invention is to provide a linear amide surfactant compound of Formula I.

Another objective of the present invention is to provide a process of synthesis of chemical entities that serve as suitable additives for warm mix asphalts.

Another objective of the present invention is to provide a warm mix asphalt formulation based on the use of suitable chemical additive.

Another objective of the present invention is to provide a cost effective warm mix asphalt formulation that ensures significant reduction of compaction temperature.

Yet another objective of the present invention is to provide a method of preparing a warm mix asphalt formulation.

SUMMARY OF THE INVENTION

Accordingly, the present invention provides chemical additives, which are liquid surfactants that act at the microscopic aggregate/binder interface to reduce internal friction during manufacturing. Thus, formulation prepared by combining these chemical additives with warm mix asphalt results in reduced compaction temperature of the bituminous mixtures without reducing their mechanical behavior.

The present invention provides an additive compound for warm mix asphalt (WMA) for pavement of road surfaces, wherein the additive is a compound of Formula I:

wherein

Formula I is 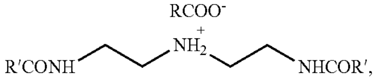, wherein R and R' are same or independently selected from $C_{12}$ to $C_{24}$ alkyl groups.

Further, the present invention provides a process for synthesis an additive compound for warm mix asphalt (WMA) for pavement of road surfaces, wherein the process comprises:

a) adding diethylene triamine to a solution of methyl stearate under stirring to obtain a reaction mixture;

b) heating the reaction mixture for 4-8 hours to obtain a brown coloured solid;

c) filtering the brown coloured solid with methanol to obtain a diamide derivative;

d) neutralizing the diamide derivative with a fatty acid to obtain the additive compound;

wherein the additive compound is represented by

Formula I as 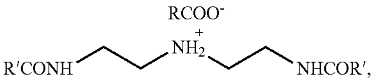, wherein R and R' are same or independently selected from $C_{12}$ to $C_{24}$ alkyl groups.

Further, the present invention provides a warm mix asphalt formulation for pavement of road surfaces, wherein the formulation comprises warm mix asphalt and an additive compound in amount ranging from 0.4 to 5% by weight of the warm mix asphalt.

DESCRIPTION OF THE INVENTION

For the purpose of promoting an understanding of the principles of the present disclosure, reference will now be made to the specific embodiments of the present invention further illustrated in specific language to describe the same. The foregoing general description and the following detailed description are explanatory of the present disclosure and are not intended to be restrictive thereof. It will nevertheless be understood that no limitation of the scope of the present disclosure is thereby intended, such alterations and further modifications in the illustrated composition, and such further applications of the principles of the present disclosure as illustrated herein being contemplated as would normally occur to one skilled in the art to which the present disclosure relates. Unless otherwise defined, all technical and scientific terms used herein have the same meaning as commonly understood by one ordinarily skilled in the art to which this present disclosure belongs. The products, methods, and examples provided herein are illustrative only and not intended to be limiting.

The present invention provides chemical additives, which are liquid surfactants that act at the microscopic aggregate/binder interface to reduce internal friction during manufacturing. Thus, formulation prepared by combining these chemical additives with warm mix asphalt results in reduced compaction temperature of the bituminous mixtures without reducing their mechanical behavior. Unlike other additives and techniques for warm-mix, the present invention does not involve an introduction of water into the mix and hence does not have any adverse effect on low temperature properties of asphalt. More specifically, the present inventors have found that a unique combination of chemical additives improves the rheological properties of the warm-mix asphalt and facilitate mixing, lay down and compaction of asphalt mixes by reducing the viscosity of the mix during the production and paving of the mix and thereby reduces the compactive effort required to attain the optimum design densities. The chemical additive of the present invention enhances the ability to compact the warm mix asphalt at a much lower temperature by the reduction of viscosity of the warm mix asphalt formulation and significantly improves the moisture resistance properties of the formulation by improving both the adhesion and cohesion properties.

Thus, the present invention provides an additive compound for warm mix asphalt (WMA) for pavement of road surfaces, wherein the additive is a compound of Formula I:

wherein

Formula I is 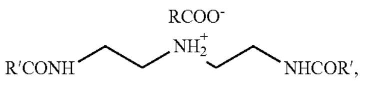

wherein R and R' are same or independently selected from $C_{12}$ to $C_{24}$ alkyl groups.

In a preferred embodiment, the present invention provides that R in Formula I is derived from stearic acid.

In a preferred embodiment, the present invention provides that R' in Formula I is a $C_{18}$ alkyl chain.

Further, the present invention provides a process for synthesis the additive compound for warm mix asphalt (WMA) for pavement of road surfaces, wherein the process comprises:

a) adding diethylene triamine to a solution of methyl stearate under stirring to obtain a reaction mixture;

b) heating the reaction mixture for 4-8 hours to obtain a brown coloured solid;

c) filtering the brown coloured solid with methanol to obtain a diamide derivative;

d) neutralizing the diamide derivative with a fatty acid to obtain the additive compound;

wherein the additive compound is represented by Formula I; as

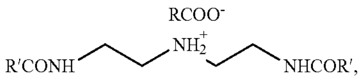

wherein R and R' are same or independently selected from $C_{12}$ to $C_{24}$ alkyl groups.

In another embodiment, the present invention provides that the fatty acid is selected from long chain acids having carbon number ranging from 12 to 24. Preferably, the fatty acid is a stearic acid.

In yet another embodiment, the reaction mixture in step (b) of the above disclosed process is heated at a temperature of 80° C.-160° C.

Further, the present invention provides a warm mix asphalt formulation for pavement of road surfaces, wherein the formulation comprises warm mix asphalt and an additive compound in amount ranging from 0.4 to 5% by weight of the warm mix asphalt.

In an embodiment, the present invention provides that the formulation comprises the additive compound selected from a compound represented by Formula I, a diester derivative of oxalic acid and a long chain alcohol, a diester derivative of sebacic acid and a long chain alcohol, or a mixture thereof;

wherein the long chain alcohol has carbon atoms ranging from 20 to 24;

wherein

Formula I is 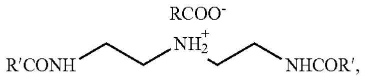

wherein R and R' are same or independently selected from $C_{12}$ to $C_{24}$ alkyl groups.

In yet another embodiment, the present invention provides that the formulation has a viscosity ranging from 50-10000 cP over a temperature ranging from 80-200° C. The viscosity of the warm mix asphalt containing the desired amount of the additive increases at lower temperature, while there is a decrease in the viscosity at higher temperatures.

In a further embodiment, the present invention provides that the temperature required to compact the formulation is 20-40° C. lower than a conventional hot mix asphalt. The use of the additives facilitates in lowering the compaction temperature of the warm mix asphalt.

In another embodiment, the present invention provides that the additive compound is blended into the warm mix asphalt in a hot-mix plant.

The present invention is further illustrated based on the disclosed embodiments through several non-limiting working examples.

Example 1: Synthesis of a Compound of Formula I

To a stirred solution of methyl stearate (2 equivalents), diethylene triamine (DETA, 1 equivalents) was added at room temperature. The reaction mixture was heated at 120° C. for 6 hours. After 6 hours, a brown color solid was obtained. The solid was filtered with methanol to obtain a diamide derivative. $^{1}H$ NMR data for the diamide derivative: 0.87 (t, 6H), 1.24-1.27 (60H), 1.61-1.79 (m, 8H), 2.15 (m, 4H), 2.71 (m, 4H), 3.32 (m, 4H), 6.1 (br s, 2H). The diamide was neutralized with the stearic acid (1 equivalents) to obtain the compound of Formula I (Compound 1). Yield: 92%.

Compound 1

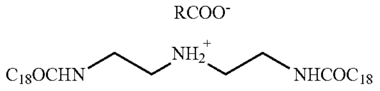

Example 2: Synthesis of a Diester Derivative of Oxalic Acid and a Long Chain Alcohol $C_{20}$ to $C_{24}$ alcohol was reacted with diacid (oxalic acid) at 70° C. in the presence of sulphuric acid for 6 hours to obtain the diester derivative of oxalic acid and a long chain alcohol (Compound 2).

Compound 2

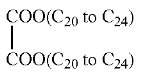

Example 3: Synthesis of a Diester Derivative of Sebacic Acid a Long Chain Alcohol $C_{20}$ to $C_{24}$ alcohol was reacted with diacid (sebacic acid) at 70° C. in the presence of sulphuric acid for 6 h to obtain the diester derivative of sebacic acid a long chain alcohol (Compound 3).

Compound 3

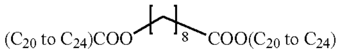

Example 4: Viscosity Measurement for Additive Performance Evaluation

The warm mix additives increase the viscosity at lower temperature when blended with warm mix asphalt and decreases the viscosity at higher temperatures.

TABLE 1

Comparison of viscosity of the disclosed formulation

| | Viscosity (cP) | | | | | |
|---|---|---|---|---|---|---|
| Temp (° C.) | Base Bitumen | Base bitumen plus 1% compound 3 | Base bitumen plus 1% compound 2 | Base bitumen plus 0.5% compound 1 and 0.5% compound 2 | Base bitumen plus 1% compound 1 | Base bitumen plus 0.1% compound 2 |
| 110 | 3634 | 5968 | 5390 | 5980 | — | 3627 |
| 120 | 2012 | 2278 | 2034 | 2974 | 2967 | 2056 |
| 130 | 1145 | 1178 | 1311 | 1385 | 1378 | 1185 |
| 140 | 722.4 | 689 | 577.9 | 920 | 911.3 | 742 |
| 150 | 466.8 | 444 | 334 | 548 | 544.6 | 440 |
| 160 | 344.5 | 256 | 233.4 | 279 | 283.4 | 320 |
| 170 | 233.4 | 155.6 | 155.6 | 182 | 178 | 220 |
| 180 | 155.6 | 77.79 | 77.79 | 94 | 92.13 | 77.79 |

From the above Table, it is inferred that warm mix asphalt formulation comprising the compound 1, 2 or 3 being mixed with the base bitumen in definite % amounts show a significant reduction in viscosity at higher temperatures. On the contrary, combination of the base bitumen with 0.1% compound 2 failed to impart the desired characteristics in the presently disclosed formulation.

We claim:

1. A warm mix asphalt formulation for pavement of road surfaces, the formulation comprising:

a warm mix asphalt;

an additive compound of Formula I, wherein

Formula I is 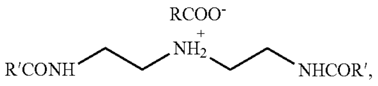

and wherein R and R' are the same or independently selected from $C_{12}$ to $C_{24}$ alkyl groups; and a diester derivative of oxalic acid and a long chain alcohol, a diester derivative of sebacic acid and a long chain alcohol, or a mixture thereof, wherein the long chain alcohol has carbon atoms ranging from 20 to 24.

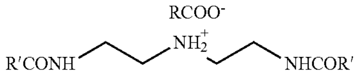

2. The formulation as claimed in claim 1, wherein the formulation has a viscosity ranging from 50-10000 centipoise (cP) over a temperature ranging from 80-200° C.

3. The formulation as claimed in claim 1, wherein the formulation has a compaction temperature that is 20-40° C. lower than a conventional hot mix asphalt.

4. The formulation as claimed in claim 1, wherein the additive compound is blended into the warm mix asphalt in a hot-mix plant.

5. The formulation as claimed in claim 1, wherein the additive compound is configured to increase viscosity of the formulation at lower temperatures and to decrease the viscosity of the formulation at higher temperatures.

6. The formulation as claimed in claim 1, wherein R in Formula I is derived from stearic acid.

7. The formulation as claimed in claim 1, wherein R' in Formula I is a $C_{18}$ alkyl chain.

8. The formulation as claimed in claim 1, wherein the additive compound is present in an amount ranging from 0.4 to 5% by weight of the warm mix asphalt.

9. The formulation as claimed in claim 1, wherein the additive compound of Formula I is synthesized according to a process comprising:

e) adding diethylene triamine to a solution of methyl stearate under stirring to obtain a reaction mixture;

f) heating the reaction mixture for 4-8 hours to obtain a brown colored solid;

g) filtering the brown colored solid with methanol to obtain a diamide derivative; and h) neutralizing the diamide derivative with a fatty acid to obtain the additive compound of Formula I.

10. The formulation as claimed in claim 9, wherein the fatty acid is selected from long chain acids having carbon number ranging from 12 to 24.

11. The formulation as claimed in claim 9, wherein the fatty acid is stearic acid.

12. The formulation as claimed in claim 9, wherein in step (b) the reaction mixture is heated at a temperature of 80° C.-160° C.

* * * * *